United States Patent [19]
Dubois

[11] Patent Number: 6,105,429
[45] Date of Patent: Aug. 22, 2000

[54] ISOLATION SYSTEM FOR A HIGH PRESSURE STEAM PIPE IN A FLOODED STRUCTURE

[75] Inventor: Neil J. Dubois, Cranston, R.I.

[73] Assignee: The United States of America as represented by the Secretary of the Navy, Washington, D.C.

[21] Appl. No.: 09/152,467

[22] Filed: Sep. 8, 1998

[51] Int. Cl.[7] ..................................................... G01M 7/00
[52] U.S. Cl. ............................................ 73/571; 73/865.6
[58] Field of Search ........................ 73/571, 570, 865.6, 73/DIG. 1

Primary Examiner—Hezron Williams
Assistant Examiner—Richard A. Moller
Attorney, Agent, or Firm—Michael J. McGowan; Prithvi C. Lall; James M. Kasischke

[57] ABSTRACT

An acoustic test assembly for testing an underwater vehicle includes a high pressure source joined by a high pressure pipe which extends into a fluid filled testing structure. A vibration shielding flange is joined to the testing structure wall where the flange supports the high pressure pipe. At least one acoustic barrier is positioned around the pipe inside the testing structure to isolate vibrations from the high pressure pipe. In further detail, the high pressure pipe is a pipe surrounded by thermal insulation and a sleeve preventing fluid from affecting the insulation. The acoustic barrier has a barrier joined by spacer means to the sleeve member.

9 Claims, 4 Drawing Sheets

ISOLATION SYSTEM FOR A HIGH PRESSURE STEAM PIPE IN A FLOODED STRUCTURE

CROSS-REFERENCE TO RELATED PATENT APPLICATION

This patent application is co-pending with two other patent applications entitled VIBRATION ISOLATING FLANGE ASSEMBLY (Ser. No. 08/976,133) and APPARATUS FOR ACOUSTICALLY ISOLATING A HIGH PRESSURE STEAM PIPE IN A FLOODED STRUCTURE (Ser. No. 09/152,466).

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

1. Field of the Invention

The present invention relates to acoustics and to a test apparatus for acoustically testing an undersea vehicle located in a flooded structure while providing the vehicle with high-pressure steam. More particularly, the present invention provides a system for isolating acoustic energy generated by the steam pipe from the structure and the surrounding fluid.

2. Brief Description of the Prior Art

Large testing structures are often used for military testing. For example, the acoustic measurement of noise caused by torpedo drive train systems is sometimes measured in large fluid filled structures into which the torpedo may be mounted and tested. During one such acoustic measurement, high pressure steam is used to power the torpedo drive train. The steam is transported from a steam generation source, through the testing structure's wall and then to the object or vehicle which is the focus of the test. In order to accurately measure noises generated by the vehicle only, vibration of the steam supply pipe must be isolated. Such vibration is caused by turbulent flow within the pipe, and may skew accuracy of acoustic measurements if allowed to effect the testing structure. Vibration isolation problems are presented by both the structure's wall and the fluid within the interior of the structure.

The prior art discloses various means for insulating pipes and tubing against the transmission of sound, heat or other forms of energy. However, the prior art does not provide for isolating the noise from the high-pressure steam traveling down the steam supply pipe from the fluid surrounding it to allow meaningful noise measurements of a vehicle under test.

SUMMARY OF THE INVENTION

A first object of this invention is providing a flooded acoustic test structure for underwater vehicles.

A second object is providing a high pressure gas or steam to such vehicles located within the acoustic test structure.

Another object is providing such a structure that is isolated from vibrations to allow precise acoustic measurements.

Accordingly, the present invention is an acoustic test assembly for testing an underwater vehicle. The assembly includes a high pressure source joined by a high pressure pipe which extends into a fluid filled testing structure. A vibration shielding flange is joined to the testing structure wall where the flange supports the high pressure pipe. At least one acoustic barrier is positioned around the high pressure pipe inside the testing structure to isolate vibrations from the pipe. In further detail the high pressure pipe is a pipe surrounded by thermal insulation and a sleeve preventing fluid from affecting the insulation. The acoustic barrier has a barrier joined by a spacer means to the sleeve member.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DESCRIPTION OF THE PREFERRED EMBODIMENT

Figure 1:
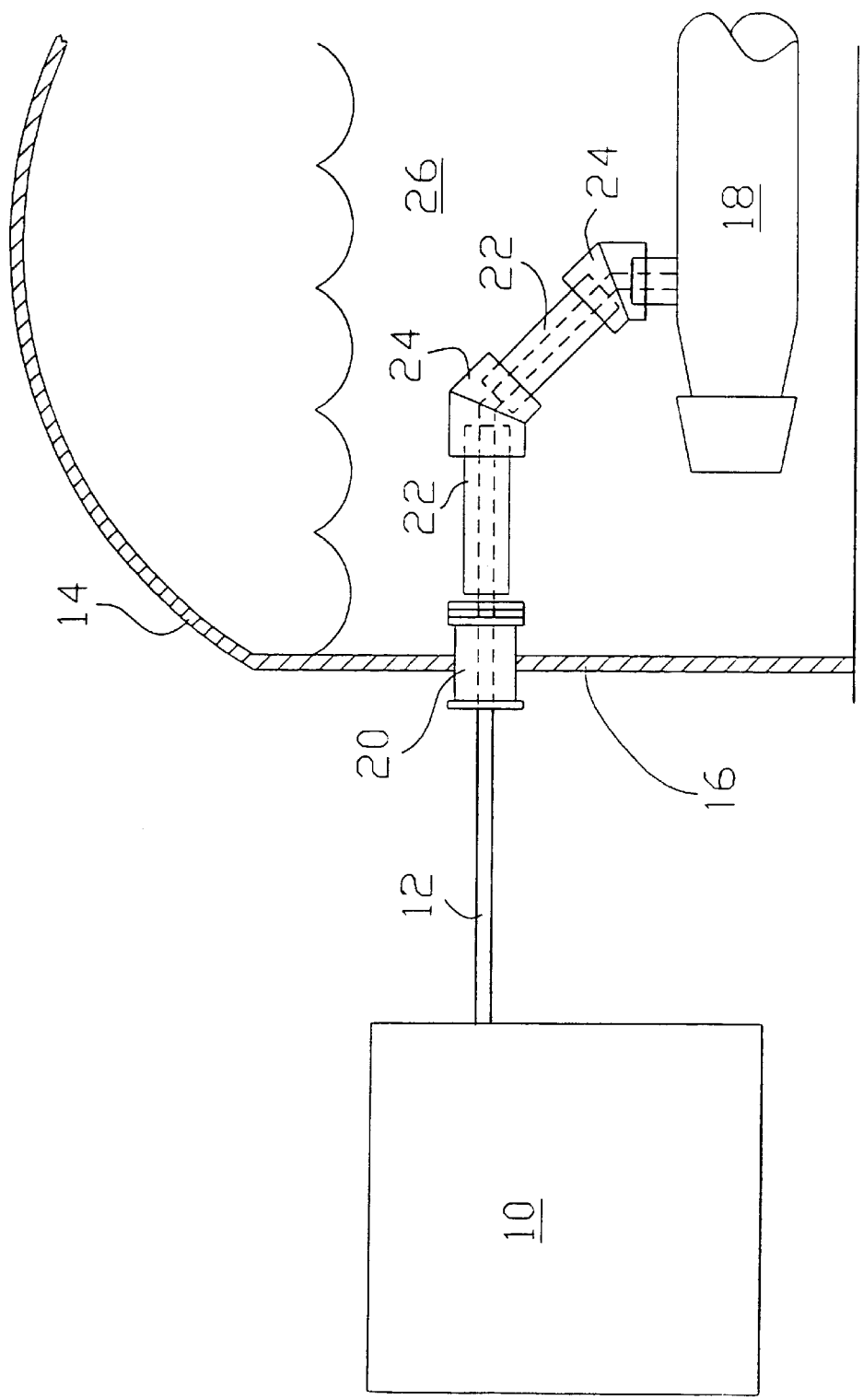
FIG. 1 is a partially cross-sectional view of the test system of the current invention.

FIG. 1 shows the test system of the current invention. The test system includes a high-pressure steam source 10 joined to a steam pipe assembly 12 which travels into a noise-testing structure 14. The steam source 10 can be any source of high pressure gas; however, in a preferred embodiment this is a high pressure steam source. The steam pipe assembly 12 passes through a wall 16 of the structure 14 and then to a vehicle 18 being tested. At wall 16 the steam pipe assembly 12 is joined to a wall flange 20. Within structure 14, vibrations from pipe assembly 12 are shielded by acoustic barrier 22. Bent acoustic barrier portions 24 are positioned about pipe assembly 12 where it has bends.

The noise-testing structure 14 is a large tank having a fluid 26 therein. The fluid 26 is typically water which can be maintained under pressure to simulate depth. Vehicle 18 is positioned inside the structure 14 and totally surrounded by fluid 26. Pipe assembly 12 is joined to provide high pressure steam to vehicle 18. Vehicle 18 can be any underwater vehicle such as a torpedo or other unmanned underwater vehicle which is adapted to operate using high pressure steam.

Figure 2:
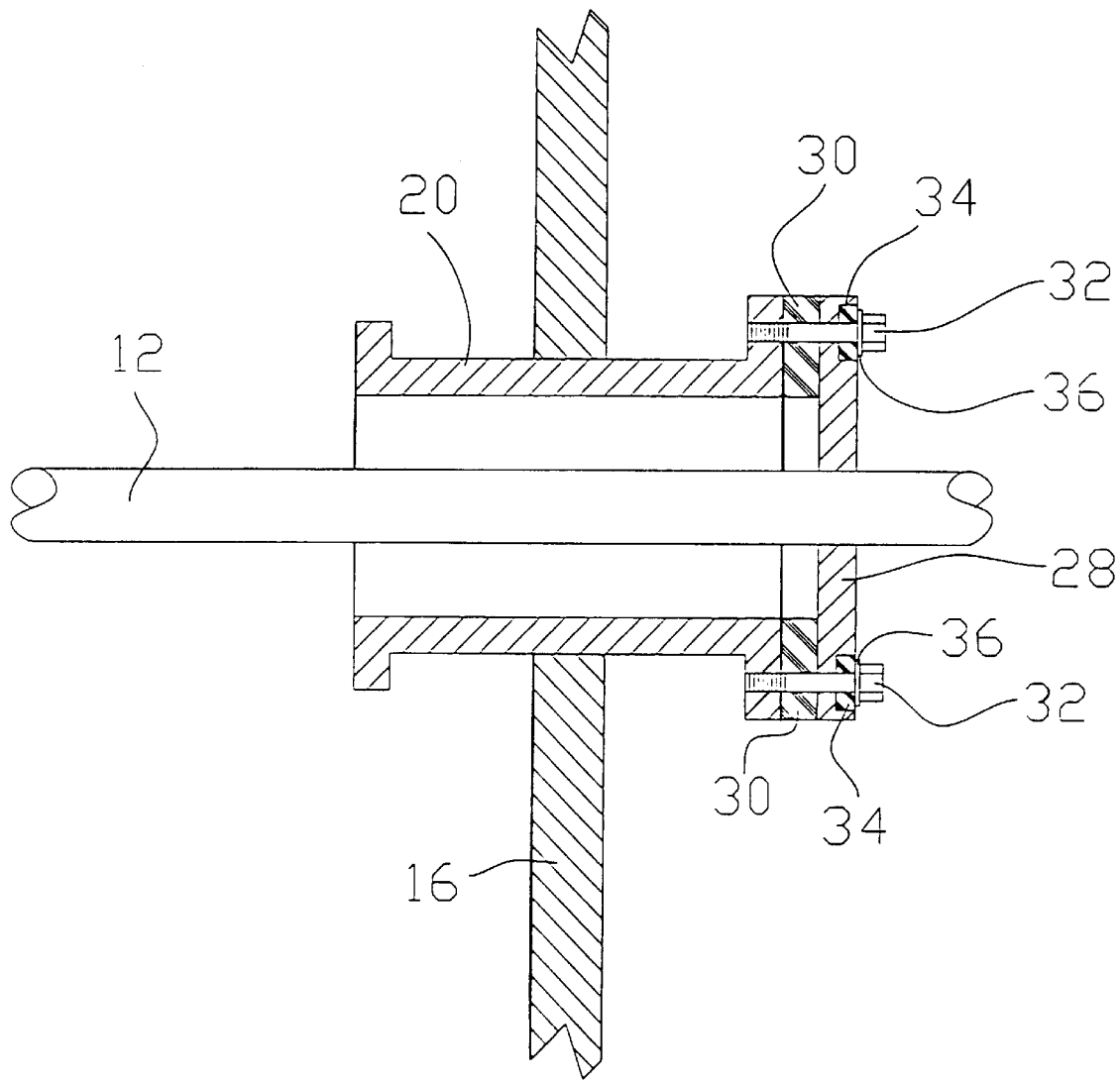
FIG. 2 is a cross-sectional view of the coupling joining the steam line to the test tank.

FIG. 2 is a cross-sectional view showing the detail of wall flange 20. The steam pipe assembly 12 passes through the wall flange 20. The wall flange 20 is commonly connected to the wall 16 by a welded connection. A pipe flange 28 is attached to the steam pipe assembly 12. A gasket 30 is provided between the pipe flange 28 and the wall flange 20 to isolate vibration occurring in pipe assembly 12. The preferred gasket material is compatible with the material of the pipe, possesses good damping properties, provides a good fluid seal, is easily moldable, is long term stable, and exhibits very little water absorption over time. One such material is the polyurethane compound Hexcel Uralite 3140 which exhibits exceptional toughness, dimensional stability, and cut resistance thereby preventing crack propagation through the gasket. Other materials may be selected according to the temperature, corrositivity, pressure, etc. of the contents of the testing chamber and the amount of damping needed.

Pipe flange 28, gasket 30 and wall flange 20 provide a seal. Gasket 30 is fastened, here by bolt 32, between the pipe flange 28 and the wall flange 20. In order to isolate vibrational energy and prevent it from traveling through the bolted connection, an annular bushing 34, preferably of the same material as the gasket 30, is provided. The annular bushing 34 is seated in a recess spaced around the pipe flange 28 with the recesses being on the side of the pipe flange 28 opposite gasket 30. A retaining washer 36, if used with bolt 32, is preferably slightly smaller in diameter than the annular bushing 34, thereby preventing metal to metal contact and transmission of vibrational energy. A fastener, here a bolt 32, tightens and ensures sealing both between the gasket 30 and the pipe flange 28 and between the gasket 30 and the wall flange 20. To join the invention together, each bolt 32 passes through an aperture in flange 28. As discussed above, bolt 32 is insulated from flange vibrations by washer 36 and bushing 34. Bolt 32 then passes through a gasket aperture corresponding to the flange aperture. The end of bolt 32 is inserted in a wall flange aperture where it can be secured by a washer and nut or by internal threading. The complete assembly thereby provides structural isolation between the pipe assembly 12 and the wall 16 while maintaining a seal against fluid leakage from inside the testing structure 14.

Figure 3:
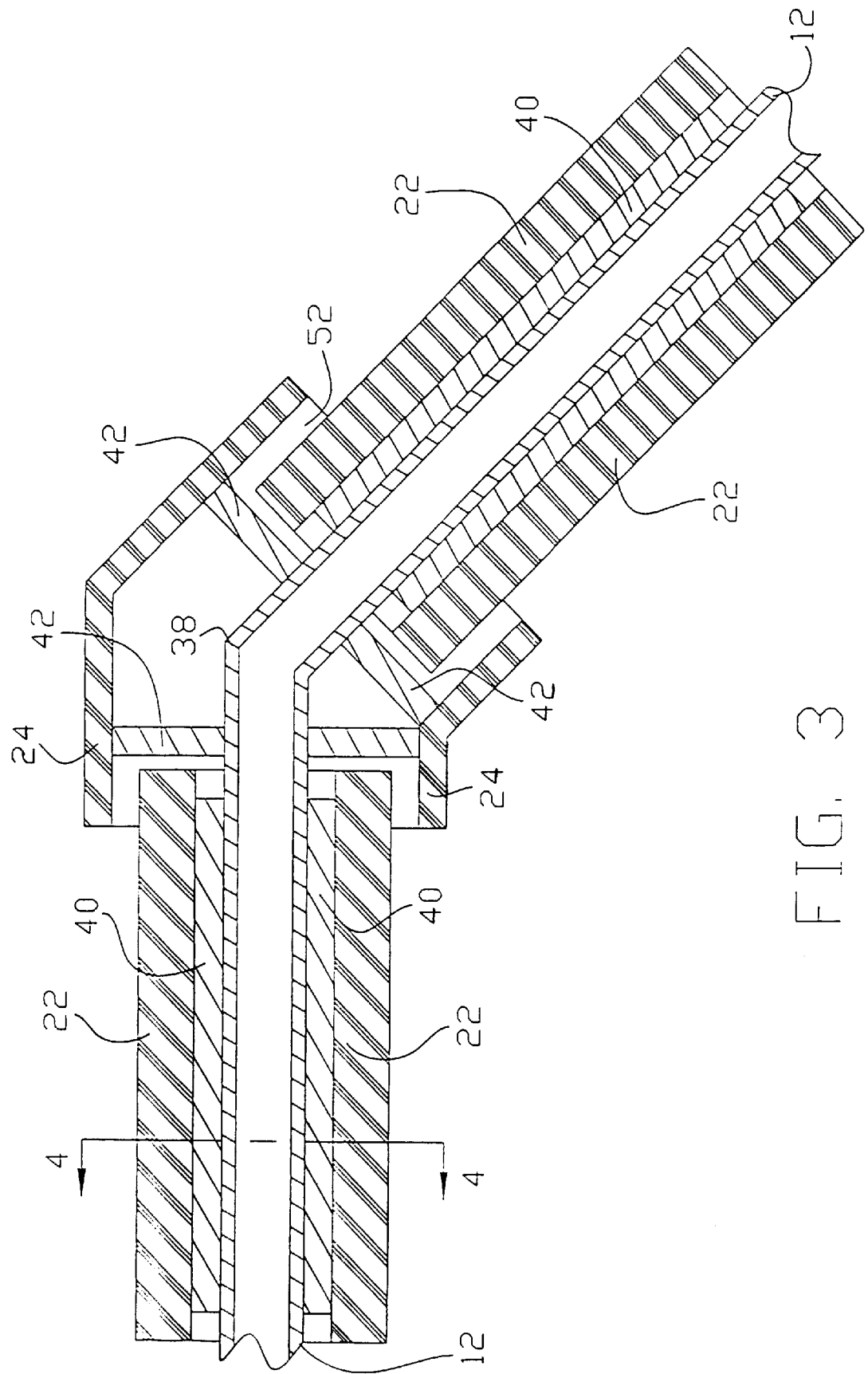
FIG. 3 is a cross-sectional view of the steam line extending through the test tank.

FIG. 3 provides a detailed cross sectional view of steam pipe assembly 12 and acoustic barriers 22 and 24. In the interior of structure 14, acoustic barrier 22 and bent acoustic barrier 24 surround the steam pipe assembly 12. Acoustic barrier 22 is cylindrical with an aperture therethrough in order to completely surround pipe assembly 12. It will be observed that there are bends 38 in the steam pipe assembly 12, and there is a gap in the acoustic barrier 22 adjacent the bend 38. Bent acoustic barrier 24 is combined from two cylindrical sections joined at an angle in order to be complementary to bend 38. The diameter of each cylindrical section is greater than the outer diameter of acoustic barrier 22. Acoustic barrier 24 covers each bend 38 and overlaps the ends of acoustic barrier 22.

Acoustic barrier 22 and bent acoustic barrier 24 are constructed of an absorptive, closed cell ionomer foam, in this case high density SOFTLITE® ionomer foam manufactured by the Gilman Corp., Gilman, Connecticut. Acoustic barrier 22 is supported at a standoff distance from the steam pipe assembly 12 by standoff 40. Bent acoustic barrier 24 is supported by another standoff distance from the steam pipe assembly 12 by standoff 42. These standoffs are segmented and allow fluid 26 surrounding the barriers to completely fill the area between the acoustic barriers 22 and 24 and the pipe assembly 12.

Figure 4:
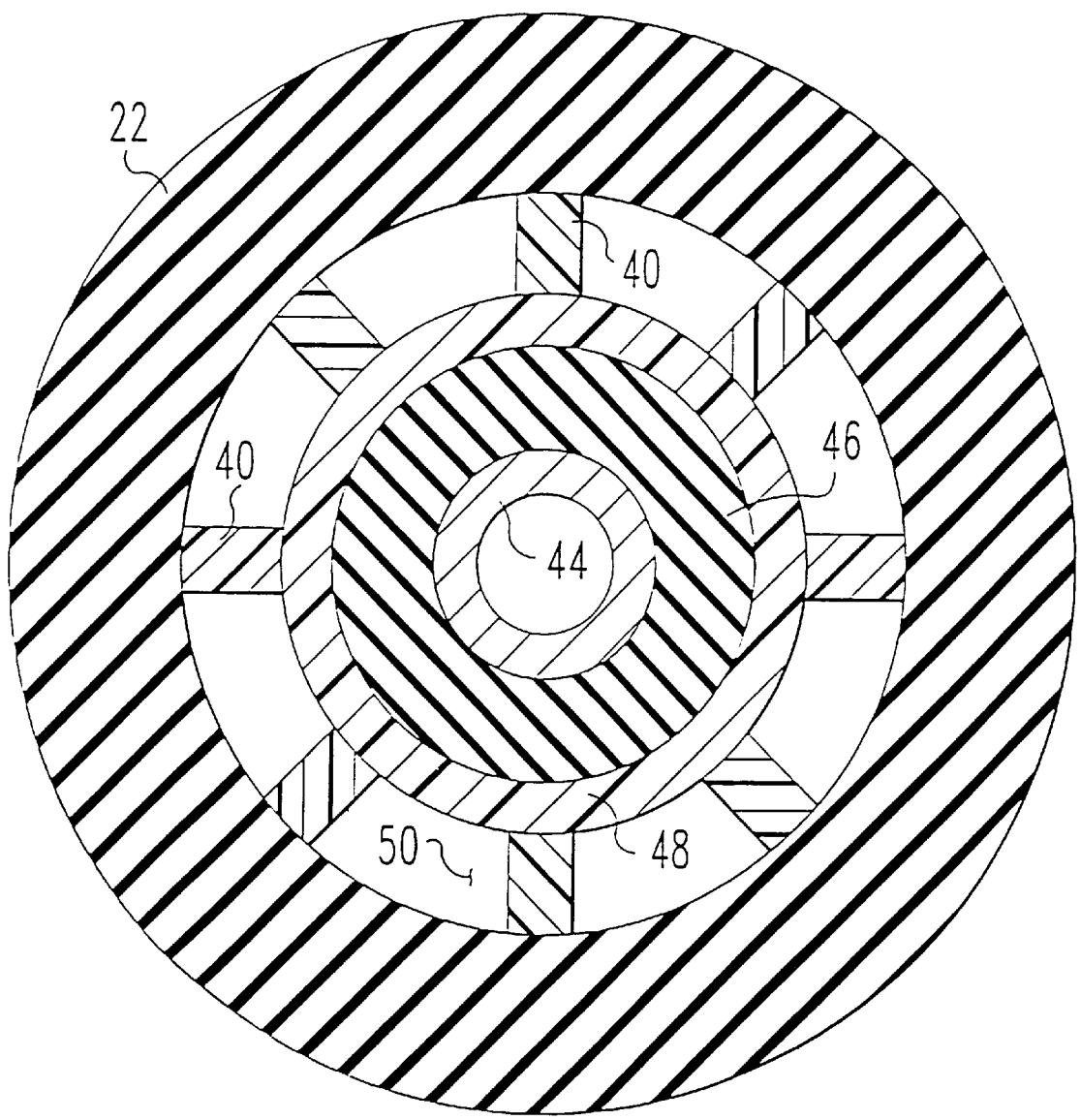
FIG. 4 is a cross-sectional view of the steam line taken along line 4—4 of FIG. 3.

Referring to FIG. 4, the purpose of the standoffs is readily apparent. The steam pipe assembly 12 includes a steel supply pipe 44, a layer of insulation 46 and a sealing sleeve of plastic 48. It will be appreciated that, for the purposes of clarity, the pipe assembly 12 is schematically shown as enlarged over that shown in FIG. 3. The layer of insulation 46 is superimposed over the supply pipe 44. The sealing sleeve 48 is superimposed over the insulation 46. The insulation 46 prevents heat transfer from the steam within supply pipe 44 to the cooler surrounding fluid thereby preventing condensation of the steam in transit. Typical pipe insulation will not hold up to water immersion, however, and thus the sealing sleeve 48 is required. In turn, fluid cooling of the plastic sleeve 48 is necessary to keep internal temperatures from surpassing the melting point of typical plastic materials, thus the fluid 26 must be allowed to contact the outside of the steam pipe assembly 12 directly. Standoffs 40 for the acoustic barriers allow free flooding of the volume 50 between sleeve 48 and acoustic barriers 22 and 24.

The acoustic barriers 22 and 24 are of different diameters and overlapped to accommodate the cooling and isolation requirements concurrently. As best shown in FIG. 3, a break 52 between barriers 22 and 24 allows for fluid to enter and fill the volume 50 between the pipe assembly 12 and the acoustic barrier 22 and 24. By overlapping the barriers 22 and 24, no direct path for acoustic energy exists between the pipe assembly 12 and the fluid medium.

The standoffs 22 and 24 are fabricated out of the same plastic used in the sealing sleeve 48 and can thus be easily bonded or welded to it. The acoustic barriers are fabricated as cylinders that are then slit lengthwise and hinged to provide a clamshell, which can be placed over the standoff assembly and then held in place with band clamps.

Those skilled in the art will appreciate that an advantage of the invention is its provision of providing a test structure that isolates acoustic energy in a high-pressure steam pipe assembly from a surrounding fluid medium to allow for high quality sound measurement. The apparatus of this invention also allows for cooling of the steam pipe assembly. The use of a high density ionomer foam allows the acoustic barriers to be fabricated as hinged cylinders with sufficient structural rigidity to maintain shape and standoff distances during the fill and empty stages of an acoustic test.

While the present invention has been described in connection with the preferred embodiments of the various elements, it is to be understood that other similar embodiments may be used or modifications and additions may be made to the present described invention without deviating therefrom. Therefore, the present invention should not be limited to any single embodiment, but rather construed in breadth and scope in accordance with the recitation of the appended claims.

What is claimed is:

1. An acoustic test assembly for testing an underwater vehicle comprising:

a high pressure source;

a high pressure pipe assembly joined to said high pressure source;

a testing structure having a wall with a communication aperture therein defining an interior portion;

a fluid contained in said testing structure interior portion for submerging said underwater vehicle therein;

a vibration shielding flange joined to said testing structure wall at said communication aperture and supporting said high pressure pipe assembly, said high pressure pipe assembly extending into said testing structure interior at said vibration shielding flange and being joined to said underwater vehicle; and at least one acoustic barrier assembly positioned around said high pressure pipe assembly in said testing structure for isolating vibrations from said high pressure pipe assembly.

2. The apparatus of claim 1 wherein:

said high pressure pipe assembly comprises:

a pipe for carrying high pressure gas;

thermal insulation means positioned radially outward from and adjacent to said pipe; and a sleeve member positioned radially outward from and adjacent to said insulation means, said sleeve member preventing communication between said fluid and said thermal insulation means; and said at least one acoustic barrier assembly comprises:

a spacer means joined to said sleeve member; and an acoustical barrier means joined outside said spacer means and surrounding said high pressure pipe assembly, said spacer means allowing environmental fluid between said sleeve member and said acoustical barrier.

3. The apparatus of claim 2 wherein the spacer means comprises a. plurality of radial standoffs longitudinally interposed between said sleeve and said acoustical barrier means.

4. The apparatus of claim 2 wherein the acoustical barrier mean's is made from an absorptive closed cell ionomer foam.

5. The apparatus of claim 2 wherein said acoustical barrier means comprises:

at least two cylinder portions made from a cylindrical portion of absorptive closed cell ionomer foam sectioned lengthwise, and a hinge portion joining said cylinder portions together longitudinally.

6. The apparatus of claim 2 wherein said acoustic barrier assembly further comprises:

a second spacer means joined to said sleeve; and a second acoustical barrier means joined to said second spacer means and positioned to overlap said acoustical barrier means in part, said second acoustical barrier means being capable of accommodating features of said pipe.

7. The apparatus of claim 6 wherein said second spacer means, said sleeve and said second acoustical barrier means define intermediate spaces and said fluid fills said intermediate spaces.

8. The apparatus of claim 1 wherein said vibration shielding flange comprises:

a pipe flange joined to said high pressure pipe assembly, said pipe flange having a first surface having a plurality of fastener recesses spaced thereabout and a second surface;

a first vibration dampening material disposed within each fastener recess;

a wall flange joined to said testing structure wall at said communication aperture;

a vibration dampening gasket disposed between the wall flange and the second surface of the pipe flange; and a plurality of fasteners, each contacting the first vibration dampening material, wherein the fasteners connect the pipe flange, the vibration dampening gasket and the wall flange for sealing the pipe flange, gasket and wall flange.

9. The apparatus of claim 8 wherein:

said high pressure pipe assembly comprises:

a pipe for carrying high pressure gas;

thermal insulation means positioned radially outward from and adjacent to said pipe; and a sleeve member positioned radially outward from and adjacent to said insulation means, said sleeve member preventing communication between said fluid and said thermal insulation means; and said at least one acoustic barrier assembly comprises:

a spacer means joined to said sleeve member; and an acoustical barrier means joined outside said spacer means and surrounding said high pressure pipe assembly, said spacer means allowing environmental fluid between said sleeve member and said acoustical barrier.

* * * * *